United States Patent [19]

Winkley

[11] Patent Number: 5,523,427
[45] Date of Patent: Jun. 4, 1996

[54] MEDROGESTONE PRODUCTION

[75] Inventor: Michael W. Winkley, St. Albans, Vt.

[73] Assignee: American Home Products Corporation, Madison, N.J.

[21] Appl. No.: 403,314

[22] Filed: Mar. 14, 1995

Related U.S. Application Data

[62] Division of Ser. No. 239,187, May 5, 1994, Pat. No. 5,428,151.

[51] Int. Cl.$^6$ ............................ C07J 75/00; C07J 5/00
[52] U.S. Cl. ............................................. 552/561
[58] Field of Search ................................. 552/561

[56] References Cited

U.S. PATENT DOCUMENTS 3,170,936   2/1965   Morand et al. .
5,428,151   6/1995   Winkley et al. .................... 540/60

OTHER PUBLICATIONS

Deghenghi et al., J. Med. Chem., 6, 301 (1963).
Yadav et al., Syn. Commun., 19 (5&6), 1057 (1989).
Carruthers et al., J. Org. Chem., 57, 961 (1992).
Posner et al., Tet. Letts., 32 (45), 6489 (1991).
Graber et al., J. Org. Chem., 27, 2534 (1962).
Bernstein et al., J. Org. Chem., 26, 269 (1961).

*Primary Examiner*—Kimberly J. Prior
*Attorney, Agent, or Firm*—Richard K. Jackson

[57] ABSTRACT

The solvate 3β,5α,6β-trihydroxy-6α,17α-dimethylpregnan-20-one monomethanolate, a crystalline intermediate in the manufacture of medrogestone, and a method for its production by displacing the solvent in a solution of 3β,5α,6β-trihydroxy-6α,17α-dimethylpregnan-20-one with methanol are disclosed.

6 Claims, No Drawings

MEDROGESTONE PRODUCTION

RELATED APPLICATION

This is a division of co-pending application, U.S. Ser. No. 08/239,187, filed May 5, 1994, now U.S. Pat. No. 5,428,151 by Michael W. Winkley and Robert D. Mitchell.

BACKGROUND OF THE INVENTION

Medrogestone (6,17α-dimethylpregna-4,6-diene-3,20-dione) is a known progestogen useful in hormone replacement therapy for inducing and reestablishing normal menstrual cycles (irregular cycles, secondary amenorrhea, oligoamenorrhea, etc.), assuring regular endometrial shedding and in arresting and controlling dysfunctional uterine bleeding (menhorrhagia, metrorrhagia, etc.). Medrogestone has been used alone and in conjunction with sequential estrogen treatment.

Medrogestone (6,17α-dimethylpregna-4,6-diene-3,20-dione) is conventionally prepared by the Grignard reaction of methyl magnesium bromide with 3β-acetoxy-5α-hydroxy-17α-methyl-17β-carbomethoxyandrostan-6-one to obtain 3β,5α,6β-trihydroxy- 6α,17α-dimethyl-17β-carbomethoxyandrostane. Upon further reaction with methyl magnesium bromide, the corresponding pregnan-20-one is obtained. The, thusly, produced pregnan-20-one is oxidized with 8N chromic acid to yield 5α,6β-dihydroxy- 6α,17α-dimethylpregnan-3,20-dione which is converted into medrogestone by acid catalyzed dehydration (U.S. Pat. No. 3,170,936 Examples 3–6). This process leads to the production of three impurities which amount to about five percent of the product. These impurities can be removed from medrogestone with some difficulty and at considerable additional expense. Hence, avoidance of the production of these byproducts during the production of medrogestone would provide a markedly improved method for the manufacture of this valuable medicinal compound.

It is currently believed that the three major contaminants formed during the preparation of medrogestone are: (1) 6,17α-dimethyl- 17β-isopropenylandrosta-4,6-dien- 3-one (generated by methylation of the 17β-methoxycarbonyl group to give the 17β-1-hydroxy-1-methylethyl substituent which is dehydrated along with the 5α- and 6β-hydroxyl groups by the conventional acid catalyzed process used in the final step of production); (2) 6-methylene-17α-methyl-pregn-4-ene-3,20-dione and (3) 6,17α-dimethylpregna-6,8(14)-diene-3,20-dione, each of which are formed as rearrangement products of the acid catalyzed dehydration of the 5α,6β-dihydroxy intermediate.

DESCRIPTION OF THE INVENTION

In accordance with this invention, them is provided a process for the production of 6,17α-dimethylpregna-4,6-diene-3,20-dione which comprises (a) isolating 3β,5α,6β-trihydroxy-6α,17α-dimethylpregnan-20-one monomethanolate from the solution of a Grignard reaction product of 3β,5α-dihydroxy-17α-methyl-17β-carbomethoxyandrostane- 6-one and a methyl magnesium halide by solvent displacement with methanol;

(b) oxidizing 3β,5α,6β-trihydroxy-6α,17α-dimethylpregnan-20-one monomethanolate to obtain 5α,6β-dihydroxy-6α,17α-dimethylpregnan-3,20-dione;

(c) dehydrating 5α,6β-dihydroxy-6α,17α-dimethylpregnan-3,20-dione under alkaline conditions to obtain 6β-hydroxy-6α,17α-dimethylpregn-4-ene- 3,20-dione;

(d) dehydrating 6β-hydroxy-6α,17α-dimethylpregn-4-ene-3,20-dione with boron trifluoride etherate at reaction and work-up temperatures below about 65° C.; and (e) isolating 6,17α-dimethylpregna-4,6-diene-3,20-dione from the diene by-product, 6-methylene-17α-methylpregn-4-ene-3,20-dione, present in the reaction product mixture from step (d) by reaction with maleic anhydride to obtain:

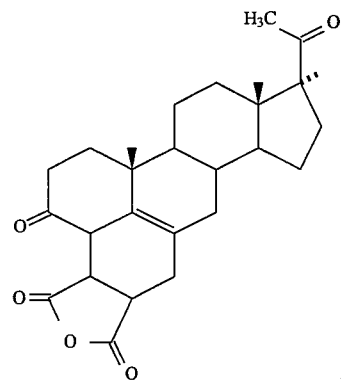

hydrolyzing the Diels-Alder adduct in the presence of a base to form the dicarboxylic acid salt:

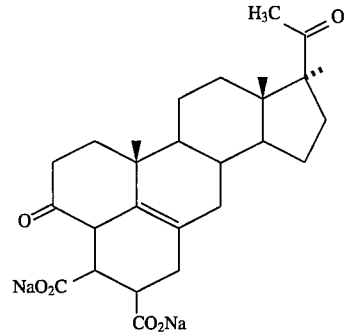

and separating of the salt by aqueous phase separation from a non-aqueous solvent containing 6,17α-dimethylpregna-4,6-diene-3,20-dione.

It has now been discovered that, by forcing 3β,5α,6β-trihydroxy-6α,17α-dimethylpregnan- 20-one from the reaction solution resulting from the methylation of 3β,5α-dihydroxy-17α-methyl-17β-carbomethoxyandrostane-6-one under Grignard conditions and drying the crystalline product thus formed, a stable monomethanol solvate is obtained free from methylated impurities. In addition, carefully controlling the dehydration of 5α,6β-dihydroxy-6α,17α-dimethylpregnan 3,20-dione under alkaline conditions in the presence of methanol, provides the novel intermediate 6β-hydroxy-6α,17α-dimethylpregn-4-ene-3,20-dione in good yields, which, unlike 5α,6β-dihydroxy-6α,17α-dimethylpregnan-3,20-dione, is readily crystallized from lower alkanols such as methanol, ethanol, isopropanol, etc., to provide pure intermediate product. Even without further purification, very little impurity appears with this new intermediate, and it is sufficiently pure to directly undergo further dehydration to Medrogestone. If the conversion of 6β-hydroxy- 6α,17α- dimethylpregn-4-ene-3,20-dione into Medrogestone is carried out with the Lewis acid, boron trifluoride etherate, rather than with the more conventional agents such as SOCl₂/pyridine, POCl₃/pyridine or MsCl/Et₃N/DMAP/CH₂Cl₂, reaction temperatures below about 65° C. are feasible and isomefization to 6,17α-dimethylpregna- 6,8(14)-diene-3,20-dione is largely avoided. Medrogestone, prepared in accordance with this invention, does contain an identifiable amount of 6-methylene- 17α-methylpregn-4-ene-3,20-dione which is readily removed by reaction of the impurity (diene) with maleic anhydride (dienophile) to produce the Diels-Alder adduct which can then be hydrolyzed in the presence of a base to afford the dibasic acid salt that is easily removed from the desired product by aqueous extraction. Medrogestone produced in accordance with the process of this invention exhibits an HPLC strength in the order of 99.2% with total impurities at about 0.08%, thereby providing a very pure therapeutic agent.

The novel process of this invention is illustrated by the following examples:

EXAMPLE 1

3β,5α,6β-Trihydroxy-6α,17α-dimethylpregnan-20-one

To a 3M solution of methyl magnesium chloride in tetrahydrofuran (1.777L, 5.33 moles) plus 50 mL tetrahydrofuran used as a transfer rinse, under a nitrogen atmosphere, cooled to 0°–5° C. was added a slurry of 3β,5α-dihydroxy-17α-methyl- 17β-carbomethoxyandrostane-6-one (200 g., 0.528 mole) in tetrahydrofuran (1.52L) over a period of 30 minutes, while maintaining the temperature below 25° C. Addition of the slurry was completed with a rinse of tetrahydrofuran (120 mL). The temperature of the vigorously stirred reaction mixture was brought to 60° C. After approximately one hour the dark solution thickened and stirring became difficult. After approximately two hours the reaction mixture became a stirrable gray slurry and it was kept at 60° C. for a total of nineteen hours. The mixture was cooled to 0°–5° C. and a solution of ammonium chloride (176.0 g) in water (700 mL) was cautiously added over a period of one hour, while maintaining the temperature below 30° C. To the resulting slurry was added water (880 mL) and the mixture was stirred for ten minutes. To the cooled mixture was added 500 mL of 12N hydrochloric acid over a period of fifteen minutes, while maintaining the temperature between 15 and 20° C. The mixture was then stirred at room temperature (23°–27° C.) for one hour. The two resulting clear phases were separated and the organic phase was washed with 80% saturated brine (2×480 mL). The organic phase was washed a third time with 80% saturated brine (480 mL) and the pH of this third wash was adjusted to pH 7 during the wash with 5% sodium bicarbonate solution. The resulting mixture of organic and aqueous phases was filtered to remove any remaining solid material and the phases were separated again. The organic phase (3,200 mL) was distilled to 1200 mL. The distillation was continued while adding methanol (2.400 L) dropwise to maintain the volume at 1200 mL while azeotropically removing most of the tetrahydrofuran solvent. The resulting slurry of crystals in methanol was allowed to cool to 30° C. over a period of 30 minutes and then cooled to 0°–5° C. over a period of 30 minutes. After forty five minutes at 0°–5° C. the crystals were collected on a filter and washed with 0°–5° C. methanol (2×200 mL). Drying under oil pump vacuum at 45°–50° C. for two hours gave 3β,5α,6β-trihydroxy-6α,17α-dimethylpregnan-20-one as a 99% pure, stable monomethanolate, m.p.=235.0°–240.5° C. High Pressure Liquid Chromatography established the purity of this product as: Strength=101.6% and Impurity=0.82%.

EXAMPLE 2

5α,6β-Dihydroxy-6α,17α-dimethylpregnan-3,20-dione

To a stirred suspension of the compound produced in Example 1 (75.0 g, 0.183 mole) in acetone (750 mL) cooled to 0°–5° C. in an ice/acetone bath, was added 158 mL (0.422 moles) of a 2.67 M solution of Jones' reagent [Reagents for Organic Synthesis, Wiley Interscience, vol. 1, page 142, 1967), while maintaining the temperature below 10° C., over a period of one hour. The addition was completed with a rinse (8 mL) of water. The resulting mixture was stirred at 0°–5° C. until the reaction was complete (about two hours) as judged by thin layer chromatography on silica gel $GF_{254}$ (E. Merck) plates with chlorofom-methanol (100:8) as developer (visualization by sulfuric acid charring). The stirred green mixture was neutralized to pH 2.5 by dropwise addition of approximately 210 mL of 6% w/w sodium hydroxide while maintaining the temperature below 5° C. The mixture was stirred at ambient temperature for half an hour. Water (565 mL) was added and the mixture was extracted with dichloromethane (450 mL and 225 mL). The combined organic extracts were washed thrice with acidified water [ first, with 565 mL $H_2O$ to which 30 mL 12N HCl was added; second, with 300 mL $H_2O$ to which 15 mL HCl was added and third, with 300 mL $H_2O$ to which 15 mL HCl was added]. The organic phase was washed with water (300 mL) and the pH of the aqueous phase was adjusted during the wash to a value of 7 with 10% $NaHCO_3$ solution. The dichloromethane solution was washed one more time with water (300 mL) and the pH of the wash checked for neutrality. The solution was distilled to a volume of 300 mL so that a thick slurry of crystals was obtained. Toluene (150 mL) was added to bring the volume to 450 mL. The mixture was distilled and the volume maintained at 450 mL by the dropwise addition of toluene (300 mL). When all the toluene had been added the volume was reduced to 300 mL and the stirred slurry was allowed to cool to room temperature over a period of two hours. After stirring the slurry at room temperature for 2 hours, the crystals were collected on a filter and washed with 0°–5° C. toluene (3×55 mL). Drying at 65° C. for 18 hours gave 63.70 g. (92.7% of theory) of 5α,6β-dihydroxy-6α,17α-dimethylpregnan-3,20-dione as a pale yellow product, having a melting point of 234.8°–237.2° C. dec. This product, 95.5% pure by HPLC, was considered sufficiently pure for conversion into 6β-hydroxy-6α,17α-dimethylpregn-4-ene-3,20-dione.

EXAMPLE 3

6β-Hydroxy-6α,17α-dimethylpregn-4-ene-3,20-dione

A mixture of the compound produced in Example 2 (620.00 g), methanol (8.00 L) and 500 mL of 5N NaOH was mechanically stirred and heated at reflux (69°–70° C. under a nitrogen atmosphere for one hour. The resulting solution was allowed to cool to 65° C. and maintained at that temperature while adding water (3,250 mL) over a period of 35 minutes. The resulting slurry of crystals was cooled to 20° C. over a period of one hour. The white crystals were collected on a filter and washed consecutively with 3:7 methanol-water (3×1 L) and water (2×1L). Drying at 80°–90° C. in a vacuum for 42 hours gave 514.98 g. (87.2% of theory) of crude product. Recrystallization of the crude product (314.62 g) from 2-propanol afforded 292.83 g. (93.1% of theory) of pure title compound; m.p=235°–237.8° C., $[\alpha]_{D=26.4°}$(c=1, $CHCl_3$); M+(DEI) 358, λ, max. (KBr) 1668, 1691 $cm^{-1}$, pmr (DMSO-$d_6$)δ5.78 (vinylic proton at C - 4). Elemental analysis for $C_{23}H_{34}O_3$ Calc'd: C, 77.05; H, 9.56 Found: C, 76.84; H, 9.49

EXAMPLE 4

6,17α-Dimethylpregna-4,6-diene-3,20-dione (Medrogestone)

A solution of the dried, unrecrystallized 6β-hydroxy-6α, 17α-dimethyl-pregn- 4-ene-3,20-dione as prepared in Example 3 (72.00 g., 0.2008 mole) in methylene chloride (650 mL) was distilled until 50 mL of distillate was collected. To the stirred, cooled (22° C.) solution under a nitrogen atmosphere was added dropwise, boron trifluoride etherate (50 mL, 0.4065 moles, 2.02 molar excess). The mixture was warmed to reflux over a period of one hour (a white crystalline complex precipitated during this time). The mixture was maintained at reflux until the reaction was complete (about one hour) as judged by thin layer chromatography on silica gel (E. Merck) plates using methylene chloride:ethyl acetate (1:1) as developer. The resulting stirred, dark red solution was cooled to 10°–15° C. using an ice bath and a slurry of $NaHCO_3$ (100g) in $H_2O$ (450 mL) was cautiously added over a period of five minutes. The two phase mixture was stirred vigorously at 10°–15° C. for one hour, at 15°–20° C. for one hour and at 20°–25° C. for thirty minutes. The layers were separated and the organic phase was washed thrice with water (250 mL). The methylene chloride solution was distilled to 150 mL (final pot temperature 50° C.) and toluene (100 mL) was added. The solution was distilled under a water aspirator vacuum to 150 mL once more. Toluene (450 mL) was added and the solution was distilled under water aspirator vacuum to a volume of 480 mL. This low temperature synthesis and work up avoids the production of 6,17α-dimethylpregna-6,8(14)-diene-3,20-dione which is believed to be a thermodynamically produced byproduct.

To the resulting toluene solution of crude product was added maleic anhydride (11.0 g, 0.1122 mole) and the mixture was heated to reflux (pot temperature 114°–115° C.) under nitrogen for one hour under Diels-Alder conditions. The cooled (22° C.) solution was added to a stirred solution of sodium carbonate (40 g) in water (720 mL) also at 22° C. and the stiffed mixture heated to 50° C. and maintained at 50° C. for one hour. The mixture was cooled to room temperature (25° C.) and the layers were separated. The organic phase was washed consecutively with 200 mL (×2) and 100 mL (×1) of 1.5 N sodium hydroxide, 300 mL of saturated brine and 200 mL (×2) of water. At this stage the aqueous washings were neutral. The solution was distilled under a water aspirator vacuum to near dryness. Heptane (250 mL) was added and the stirred mixture was heated to reflux (98°–99° C.) under nitrogen. The resulting solution was allowed to cool and the title compound crystallized by appropriate seeding. Crystallization started at 78° C. When the temperature of the stirred slurry of crystals reached 35° C. ice/water cooling was used to lower the temperature to 0°–5° C. The crystals were collected on a filter and washed with heptane (2×75 mL); 55.2 g, (80.8% of theory).

Three crystallizations from 2-propanol afforded pure material (38.03 g, 55.6%) having a m.p.=145°–147° C., $[\alpha]_D=77.7°$ (c=1, $CHCl_3$), $M^{+(PBEI)}$ 340 and λmax. (KBr) 1665, 1691 $cm^{-1}$. Elemental analysis for $C_{23}H_{32}O_2$ Calc'd: C, 80.94; H, 9.26 Found: C, 80.90; H, 9.28

In addition to the novel process, it has been found that the novel intermediate, 6β-hydroxy-6α,17α-dimethylpregn-4-ene-3,20-dione is useful in preventing smooth muscle cell proliferation. This utility was established by subjecting the compound to the following standard experimental test procedure:

Primary rat aorta smooth muscle cell cultures grown in media 199 (Gibco) plus 10% fetal bovine serum (Gibco) were washed with calcium, magnesium free Dulbecco's phosphate buffered saline and trypsinized for five minutes. Cells were scraped from culture dishes with a rubber policeman and centrifuged. Cells were resuspended in M199 plus 10% fetal bovine serum containing [$^3$H]-thymidine (0.5 µCi/mL) at 8–15,000 cells/mL, and were placed into plate wells. The novel intermediate was added to each well and the plates were incubated for 24 hours at 37° C. in a 5% $CO_2$ atmosphere. The cultured cells were treated with trichloracetic acid to remove acid soluble proteins, leaving only cell superstructure and DNA. These cells were solubilized, counted by scintillation and the results compared with control to determine the number of cells per well, the difference in cells being expressed as a percent of control. Based upon this study, 6β-hydroxy-6α,17α-dimethylpregn-4-ene-3,20-dione demonstrated an $IC_{50}$ of 26.45 µM whereas Medrogestone demonstrated an $IC_{50}$ of 14.84 µM.

Hence, the compound, 6β-hydroxy-6α,17α-dimethyl-pregn-4-ene- 3,20-dione, as an inhibitor of smooth muscle proliferation, is useful in the treatment of restinosis and atherosclerosis and it and pharmaceutical compositions containing it, present additional aspects of this invention. The pharmaceutical compositions involved may be administered by any route conventionally employed with steroids, for example, transdermally, orally. parenterally, intranasally, etc. The steroid may be administered neat or in combination with a pharmaceutically acceptable carrier.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a phamaceutically acceptable liquid carder such as water, an organic solvent, a mixture of both or pharmaceutically acceptable oils or fats. The liquid carder can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carder for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The dosage requirements will vary with the route of administration, the severity of the symptoms presented and the particular subject being treated. Based on the results obtained in the standard pharmacological test procedure, projected daily dosages of 6β-hydroxy-6α,17α-dimethyl-pregn-4-ene-3,20-dione, would be 0.005–50 mg/kg and preferably between 0.05–10 mg/kg.

Treatment will generally be initiated with small dosages less than the optimum dose of the compound. Thereafter the dosage is increased until the optimum effect under the circumstances is reached; precise dosages for oral, parenteral, intranasal, or transdermal administration will be determined by the administering physician based on experience with the individual subject treated.

What is claimed is:

1. A process for the production of 3β,5α,6β-trihydroxy-6α,17α-dimethylpregnan- 20-one monomethanolate which comprises displacing the organic solvent from a solution of 3β,5α,6β-trihydroxy-6α,17α-dimethylpregnan-20-one with methanol.

2. The process of claim 1 in which said 3β,5α,6β-trihydroxy-6α,17α-dimethylpregnan- 20-one monomethanolate is collected from a slurry in methanol as a crystalline product and subjected to a drying atmosphere to drive off excess methanol.

3. The process of claim 1 in which the solvent displaced from 3β,5α,6β-trihydroxy- 6α,17α-dimethylpregnan-20-one by methanol is tetrahydrofuran, as an azeotropic mixture.

4. The process of claim 2 in which said drying atmosphere is produced by a reduced atmospheric pressure at a temperature between ambient temperature and about 60° C.

5. The process of claim 4 in which said reduced atmospheric pressure is an oil pump vacuum created atmosphere.

6. The solvate 3β,5α,6β-trihydroxy-6α,17α-dimethylpregnan-20-one monomethanolate.

* * * * *